Nov. 5, 1957 E. S. BOERNER Plant Pat. 1,657
CHRYSANTHEMUM PLANT
Filed March 1, 1957
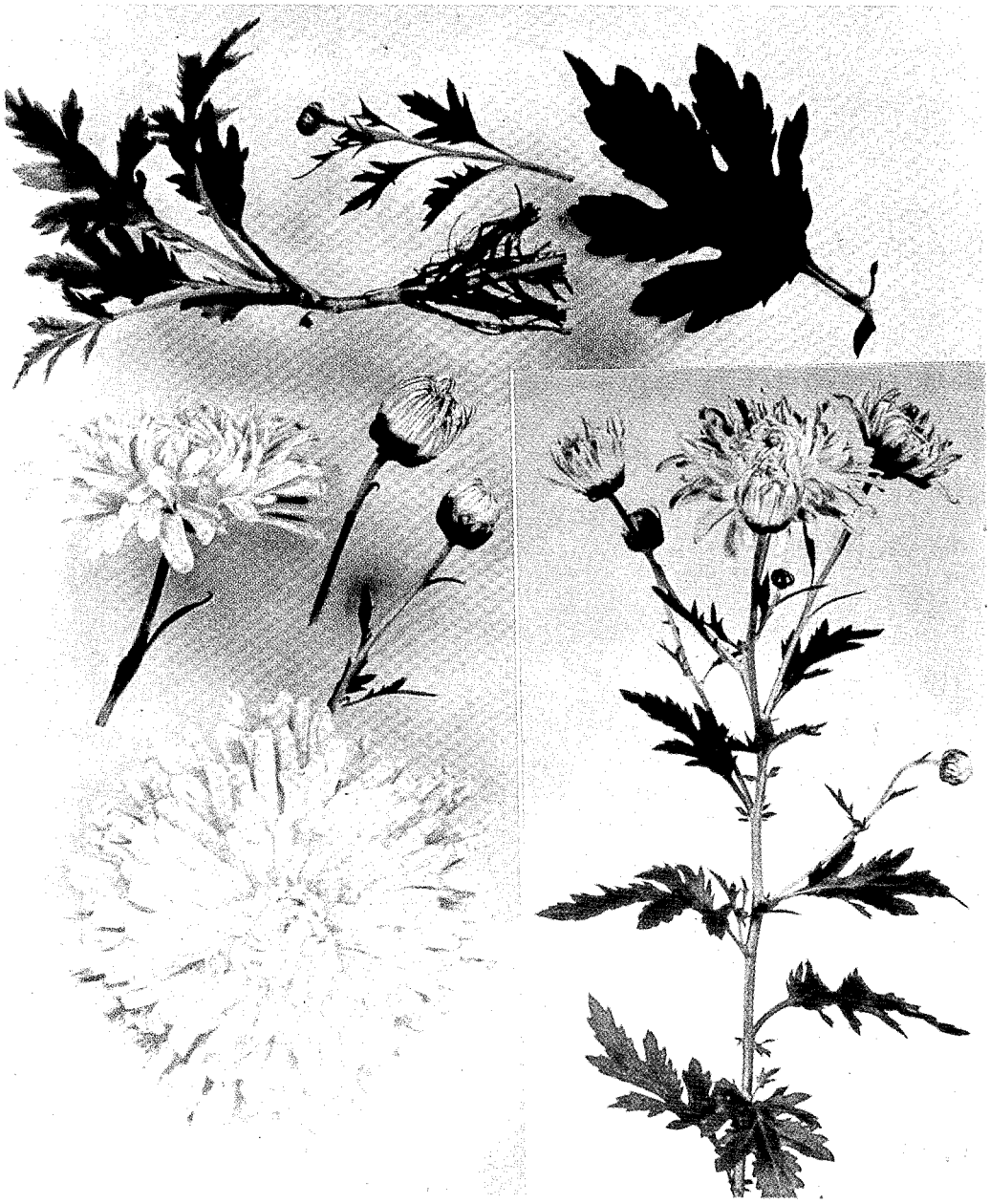
Inventor.
E. S. Boerner
By: Robert Cobb
Attorneys.

United States Patent Office

Plant Pat. 1,657
Patented Nov. 5, 1957

1,657

CHRYSANTHEMUM PLANT

Eugene S. Boerner, Newark, N. Y., assignor to Jackson & Perkins Company, Newark, N. Y., a corporation of New York Application March 1, 1957, Serial No. 643,481

1 Claim. (Cl. 47—60)

The present invention relates to a new and distinct variety of chrysanthemum plant of the decorative type, which was originated by me by crossing an unnamed and unpatented seedling derived from a cross of "Meadowlark" (Plant Patent No. 1,305)×"Thrush" (Plant Patent No. 1,168) with the variety named "Goldfinch" (Plant Patent No. 1,166).

The primary objective of this breeding was to produce a new chrysanthemum variety having the flower size and color of the parent "Goldfinch," combined with the sturdy and vigorous plant habits of the other seedling parent aforementioned. This objective was fully achieved, along with other improvements, as evidenced by the following characteristics which are outstanding in the new variety:

(1) The sturdy and vigorous growth;

(2) The strong stems and evenly clustered flowers at the top thereof;

(3) The large size of the flowers;

(4) The Light Cadmium, lightly overcast with Deep Chrome, general color tonality of the flowers; and (5) The Dark Green general color tonality of the foliage which strikingly contrasts with the color of the flowers.

The foregoing characteristics and distinctions definitely differentiate the new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character, as well as a typical specimen plant which is depicted in black-and-white as illustrative of the form and habit of growth of the plant.

The following is a detailed description of my new variety, with color terminology in accordance with Ridgway's Color Standards and Nomenclature, as based upon observations made from specimens grown outdoors at Newark, New York, about mid-morning in the latter part of the month of September:

Parentage: An unnamed seedling derived from a cross of "Meadowlark"×"Thrush"×"Goldfinch."

Classification: Decorative, with incurved petals in center of flower.

Growth: Upright; attains a height averaging about 27 inches.

Cold resistance: Plants are very winter hardy in northern New York, and flowers are frost resistant.

Blooming period: In the Newark, New York climatic area, blooming begins at the end of September and continues until heavy frosts.

*Flower*

Bud:

*Color.*—When sepals first divide—Pale Lemon Yellow, Plate 4. When petals begin to unfurl—Picric Yellow, Plate 4, in lower half of petal; Flesh color, Plate 14, in upper half of petal. When half-blown: inside of petals—Lemon Chrome, Plate 4, with center of petal overcast with Orange Buff, Plate 3; reverse of petals—Empire Yellow, Plate 4, with lower half of petal lightly overcast with Deep Chrome, Plate 3.

*Peduncle.*—Strong. Color—Cress Green, Plate 31.

Bloom:

*Size.*—4½ inches.

*Stem.*—Strong; with evenly clustered flowers at the top.

*Form.*—Decorative; with incurved petals in center of flower.

*Petalage.*—Double.

*Color.*—Center of flower—Light Cadmium, Plate 4, lightly overcast with Deep Chrome, Plate 3. Outer petals—Apricot Yellow, Plate 4, lightly overcast with Empire Yellow, Plate 4. Base of petals—Clear Dull Green-Yellow, Plate 17. Inside of petals—Light Cadmium, Plate 4, faintly overcast with Deep Chrome, Plate 3. Reverse of petals—Pinard Yellow, Plate 4.

*Petals.*—Texture—thick. Form—oval.

*Fragrance.*—Characteristic chrysanthemum.

*Plant*

Form: Upright; compact.

Growth: Free; vigorous.

Foliage:

*Size.*—Medium.

*Quantity.*—Normal.

*Color.*—Upper side—Dark Cress Green, Plate 31. Reverse side—Light Elm Green, Plate 17.

*Texture.*—Leathery.

I claim:

A new and distinct variety of chrysanthemum plant of the incurved-center-petal decorative type, substantially as herein shown and described, characterized particularly as to novelty by its sturdy and vigorous plant growth, its strong stems which bear evenly clustered flowers at the top thereof, the relatively large size of its flowers, the Light Cadmium lightly overcast with Deep Chrome general color tonality of its flowers, and the contrasting Dark Green color of its foliage.

No references cited.